(12) United States Patent
Mikus et al.

(10) Patent No.: US 6,419,690 B1
(45) Date of Patent: Jul. 16, 2002

(54) URETHRAL WARMING CATHETER

(75) Inventors: Paul W. Mikus, Irvine; K. David Crockett, Los Angeles, both of CA (US)

(73) Assignee: Endocare, Inc., Irvine, CA (US)

( * ) Notice: Subject to any disclaimer, the term of this patent is extended or adjusted under 35 U.S.C. 154(b) by 0 days.

(21) Appl. No.: 09/491,198

(22) Filed: Jan. 25, 2000

Related U.S. Application Data

(63) Continuation of application No. 08/816,913, filed on Mar. 13, 1997, now Pat. No. 6,017,361.

(51) Int. Cl.[7] ................................................. A61F 7/00
(52) U.S. Cl. ...................... 607/105; 607/140; 607/113; 606/20; 606/27; 606/28
(58) Field of Search ................................. 607/101, 102, 607/104, 105, 113, 115, 116, 122, 149, 154; 606/27, 28, 20, 21, 22, 23, 24, 25, 26

(56) References Cited

U.S. PATENT DOCUMENTS

| 5,437,673 A | * | 8/1995 | Baust et al. .................. 604/30 |
| 5,653,692 A | * | 8/1997 | Masterson et al. .......... 604/113 |
| 5,957,962 A | * | 9/1999 | Wallsten et al. ............... 606/27 |

* cited by examiner

Primary Examiner—Linda C. M. Dvorak
Assistant Examiner—Kenneth G Schopfer

(57) ABSTRACT

A warming catheter for use during cryosurgical ablation of the prostate having a warming section with diffuser ports promoting even warming of the prostatic urethra; the warming catheter is also provided with a short monorail lumen, monorail tip lumen, or a full length monorail lumen.

15 Claims, 4 Drawing Sheets

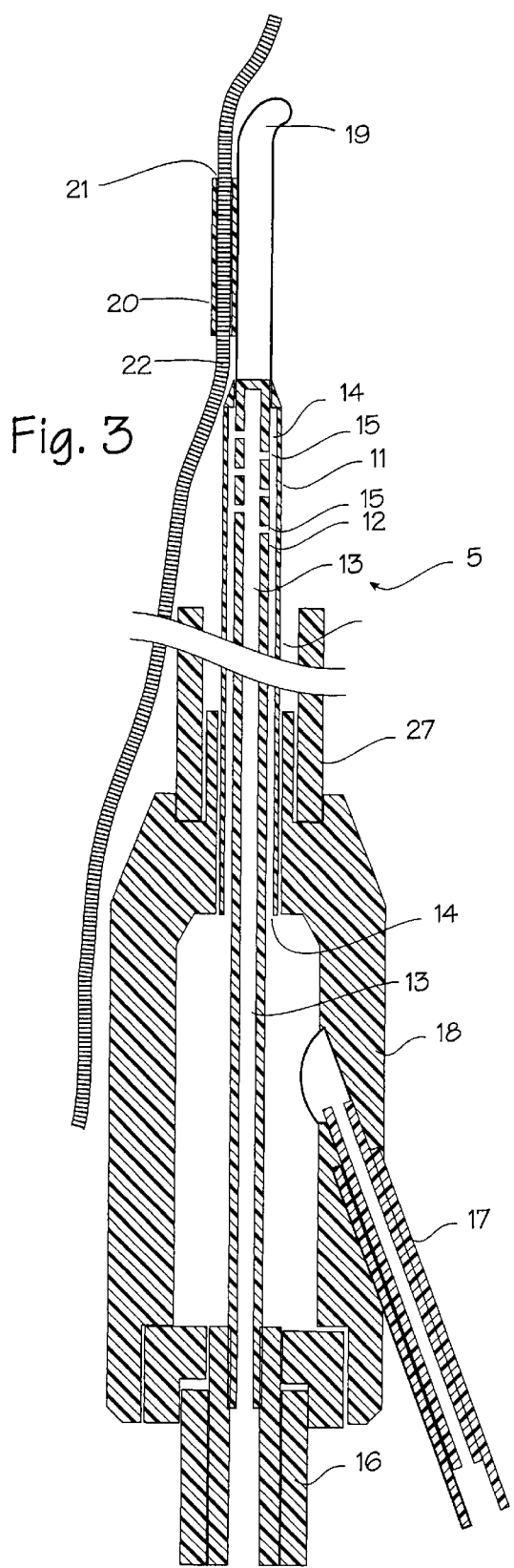
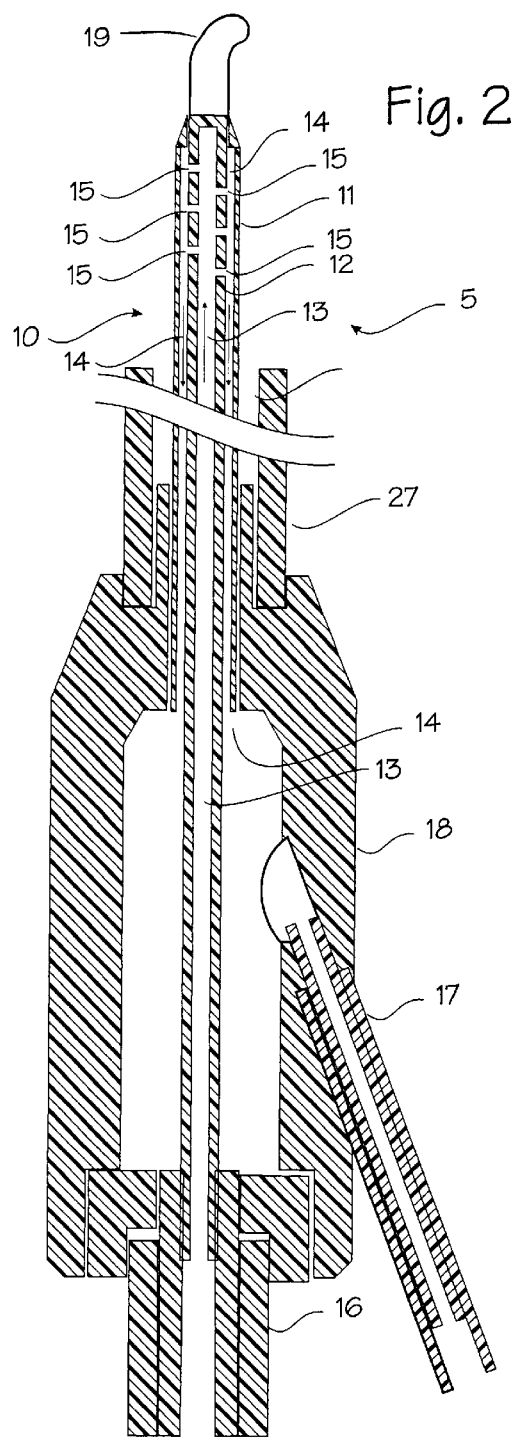

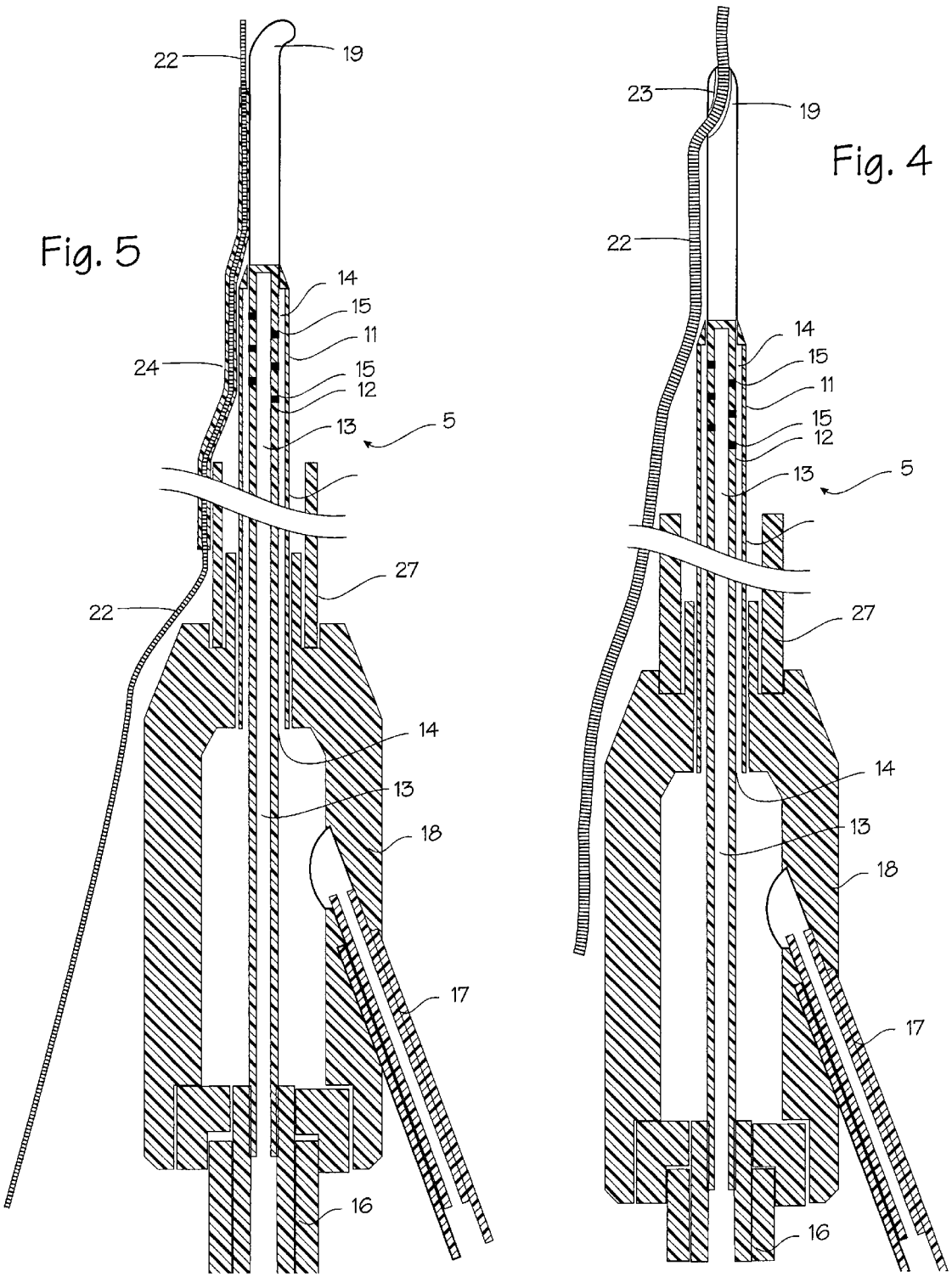

URETHRAL WARMING CATHETER

This application is a continuation of U.S. App. Ser. No. 08/816,913 filed Mar. 13, 1997, now U.S. Pat. No. 6,017,361.

FIELD OF THE INVENTION

This invention relates to urological warming devices.

BACKGROUND OF THE INVENTION

Cryosurgical probes are used to treat a variety of diseases. The cryosurgical probes quickly freeze diseased body tissue, causing the tissue to die after which it will be absorbed by the body, expelled by the body or sloughed off. Cryothermal treatment is currently used to treat prostate cancer and benign prostate disease, breast tumors and breast cancer, liver tumors and liver cancer, glaucoma and other eye diseases. Cryosurgery is also proposed for the treatment of a number of other diseases.

The use of cryosurgical probes for cryoablation of the prostate is described in Onik, Ultrasound-Guided Cryosurgery, Scientific American at 62 (January 1996) and Onik, Cohen, et al., Transrectal Ultrasound-Guided Percutaneous Radial Cryosurgical Ablation Of The Prostate, 72 Cancer 1291 (1993). In this procedure, generally referred to as cryoablation of the prostate, several cryosurgical probes are inserted through the skin in the perineal area (between the scrotum and the anus) which provides the easiest access to the prostate. The probes are pushed into the prostate gland through previously placed cannulas. Placement of the probes within the prostate gland is visualized with an ultrasound imaging probe placed in the rectum. The probes are quickly cooled to temperatures typically below −120° C. The prostate tissue is killed by the freezing, and any tumor or cancer within the prostate is also killed. The body absorbs some of the dead tissue over a period of several weeks. However, other necrosed tissue may slough off and pass through the urethra, often causing undesirable blockage. Thus, it is often desirable to avoid cryoinjury to the urethra during cryoablation of the prostate. This may be done by placing a warming catheter in the urethra and continuously flushing the catheter with warm fluid to keep the urethra from freezing.

Devices for warming the urethra have been available for quite some time. In 1911, U.S. Pat. No. 1,011,606 issued for an "Appliance For Subjecting Portions of The Human System To Heat Or Cold." This device was a coaxial dual lumen catheter intended for the application of therapeutic cooling or heating to the urethra and bladder. Devices for warming other body parts have also been proposed, such as Grams, Ear Probe For Use In Closed-Loop Caloric Irrigation, U.S. Pat. No. 4,244,377 (Jan. 13, 1981), which shows a coaxial dual lumen cannula intended for the application of therapeutic heating inside the ear. Baust, et al., Closed Circulation Tissue Warming Apparatus and Method of Using the Same in Prostate Surgery, U.S. Pat. No. 5,437,673 (Aug. 1, 1995), and related publications, illustrate use of a urethral warming catheter which is used to protect the urethra from cryothermal damage during cryosurgical treatment of the prostate for benign prostate hyperplasia. The Baust patent discloses a coaxial three lumen catheter in which warm saline passes through the outside lumen, returns through a coaxial second lumen, while the third lumen is a urinary drainage lumen centrally disposed within the other two lumens. The catheter is used to heat the urethra while the prostate is being frozen with cryosurgical probes.

Eshel, Technique for Localized Thermal Treatment of Mammals, U.S. Pat. No. 5,257,977 (Nov. 2, 1993) shows a catheter which delivers heated saline flow to provide therapeutic hyperthermia treatment of the prostate. Like the Baust patent, Eshel shows a three lumen catheter with centrally located urinary drainage lumen.

Still other devices have been described for importing fluid into the body and allowing a means for removing fluid from the body. One such device is described in Schossow, Endotracheal Tube, U.S. Pat. No. 3,087,493 (Apr. 27, 1960). Schossow describes a device employed to intubate the human trachea, such device connected with ducts and/or tubes outside the patient for the purpose of, for example, drawing off from the patient's respiratory tract undesirable liquids and/or introducing beneficial liquids into the trachea. The device consists of an outer tube, which fits inside the patient's trachea, and a two layered inner tube. The lumen of the inner tube is open to be connected with devices or ducts through which suction may be applied or fluids injected into the trachea. The distal portion of the inner tube is vented with ports or openings which create a "sprinkler" effect inside the tube. Schossow does not suggest use as a urethral warming catheter during cryoablation of the prostate.

During cryoablation, the prostate tissue is killed by freezing temperatures in the cryogenic temperature range, typically −120° C. and below. The hot fluid used for the warming catheter is supplied at about 30° C. to 50° C. Warm fluid is pumped through the urethral warming catheter, such as the catheter described in Baust. As the warm fluid travels the length of the urethral catheter disposed within the cryosurgically cooled urethra, it is cooled by the surrounding freezing tissue. By the time the hot water has traveled from the bladder neck sphincter to the external sphincter, it has been significantly cooled by the surrounding frozen prostate. As a result, the urethral tissue near the bladder neck sphincter (near the hot water outlet) is heated more than the urethral tissue near the external sphincter, creating a strong thermal gradient in the prostatic urethra and an uneven heating effect. By the time the hot water reaches the external sphincter, it may have lost so much heat to the upper region of the urethra that it is not warm enough to protect the external sphincter from freezing. In order for the tissue at the bladder neck sphincter to be adequately warmed, hotter water must be pumped in, risking urethral damage due to scalded tissue, or more water must be pumped at higher rates and pressures, increasing the material requirements of the hot water supply system and the warming catheter.

Another practical problem that arises in the current design of urethral warming catheters is that there is no provision for the use of a guide wire to assist in placement of the warming catheter. The warming catheter must be inserted into the urethra in order to protect the urethra during cryoablation. Insertion of the catheter may be difficult, especially if the urethra is blocked. This often occurs because the prostate is swollen, and the swollen prostate pinches the urethra shut, or because of some undesired tissue growth within the urethra which accompanies the underlying BPH or prostate cancer condition.

Yock, Angioplasty Apparatus Facilitating Rapid Exchange and Method, U.S. Pat. No. 5,501,227 (Mar. 26, 1996) describes an apparatus for inserting a balloon angioplasty catheter into a patient's blood vessel. It consists of a balloon angioplasty catheter with a monorail or side saddle lumen placed distal to the angioplasty balloon. This lumen accepts a guide wire which may be threaded into the lumen. After the guide wire is placed in the blood vessel, the back end of guide wire is threaded into the monorail lumen, and the catheter is then pushed along the guide wire until it is in place within the blood vessel. Yock does not suggest use during cryoablation of the prostate or use within the urethra.

SUMMARY

The devices described below provide an improved method and means for maintaining the temperature of urethral tissues during cryoablation of the prostate gland and thereby eliminates or reduces the sloughing of dead cells into the urethra. Diffuser holes or ports, much like a "sprinkler," are drilled into the inner tube of the warming catheter. The holes create an advantage over the prior art of achieving improved uniformity of fluid flow and temperature, utilizing a lower initial temperature and resulting in a more even application of thermal treatment to the urethral tissues. The apparatus may find additional utility in other areas of surgery where thermal treatment or maintenance of tissues is required with or without the capability of drainage.

The devices also provide an improved means for introducing the warming catheter into the human body. The device employs a monorail sleeve or guide-eye on the distal end of the catheter such that the proximal end of the guidewire can be slipped through the monorail sleeve of the catheter. The various configurations of the monorail sleeve and monorail tip may be employed to deliver the catheter.

BRIEF DESCRIPTION OF THE DRAWINGS

FIG. 2 is a cross-sectional view of the warming catheter.

FIG. 3 is a cross-sectional view of the warming catheter with a monorail sleeve.

FIG. 4 is a cross-sectional view of the warming catheter with a monorail tip.

FIG. 5 is a cross-sectional view of the warming catheter with a monorail tip.

DETAILED DESCRIPTION OF THE INVENTION

Figure 1:
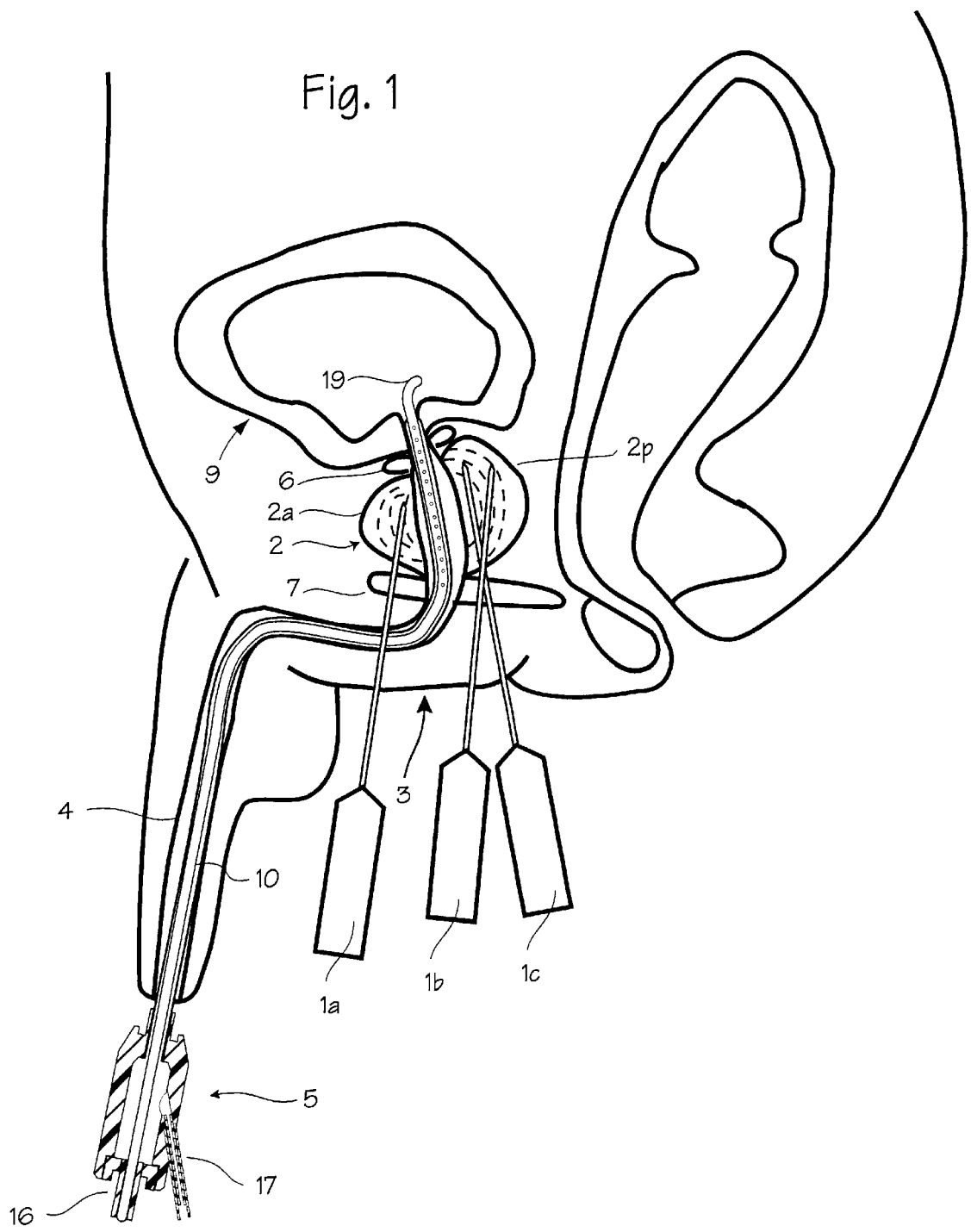
FIG. 1 is a cross-sectional view of the lower abdominal portion of the human body with the warming catheter in place.

FIG. 1 shows one of the basic operations for which the warming catheters are designed. Several cryosurgical probes 1a, 1b, and 1c are shown inserted in the prostate 2. All three probes are inserted through the perineal region 3 between the scrotum and the anus. Probe 1a is shown inserted into the anterior lobe 2a of the prostate, and probes 1b and 1c are shown inserted into the posterior lobe 2p, which is larger than the anterior lobe. The probes are placed within the prostate according to procedures well known in the art, and a suitable procedure is described in step-by-step detail in Onik, et al., Percutaneous Prostate Cryoablation, (1995) at pages 108–112 and Onik, Ultrasound-Guided Cryosurgery, Scientific American at 62. (January 1996). According to these references, the urethra 4 which passes through the prostate is one of the anatomic structures that usually should not be frozen during this surgery. Accordingly, the urethra is protected and kept warm with the urethral warming catheter 5. In the warming catheters described above, hot water is discharged from an inner lumen of catheter at a point near the bladder neck sphincter 6 and flows proximally through the outer sleeve, and the hot water flows through an outer lumen in the proximal direction through the prostate, past the external sphincter 7 and continues to the proximal end of the warming catheter.

FIG. 2 shows the warming catheter assembly 5. The overall length of the catheter is about 35 cm long. The warming catheter has urethral insertion portion 10 which is about 30 cm long, so that it may be inserted in the urethra and reach the prostate, as illustrated in FIG. 1. The urethral insertion portion 10 has coaxial or concentric outer and inner tubes, the outer tube 11 and the inner tube 12 forming inner lumen 13 within the inner tube and an outer lumen 14 between the inner and outer tubes. A fluid path is formed between the inner lumen and the outer lumen. In order to form the return fluid path and thereby provide a fluid return from the inner lumen through outer lumen, the distal end of outer sleeve is reduced and sealed to inner tube 12 adjacent the distal end thereof, preferably several centimeters from the distal end. The lumen of the inner tube may terminate at the seal. Several diffuser ports 15 provide a fluid flow path between the inner lumen and the outer lumen so that fluid introduced into inner lumen through inflow port 16 may pass out of the inner lumen into outer lumen and return the length of catheter to outflow port 17. The diffuser ports are provided at the distal end of the inner tube 12 which will be located inside the prostatic urethra during use. The outer and inner sleeves are preferably made from a flexible, relatively non-stretchable, polyester film such as polyethylene terephthalate, outer sleeve having a fixed diameter upon introduction of fluid into the outer lumen. Preferably, the outer diameter is about 22 French, which corresponds to the average diameter of the urethra in adult male humans. The diameter may be slightly larger than the urethra, allowing for some distention of the urethra during insertion and ensuring a tight fit and conformance between the outer tube and the urethra. In some instances, as in pathologically tortuous urethras, an elastic outer sleeve may be provided so that, when pressurized, it conforms to the urethra. The handle 18 houses the inflow port and outflow port. The distal tip 19 of the warming catheter is provided with a flexible atraumatic tip which may be curved in the fashion of a coude tip, which helps in navigating the warming catheter through the urethra during insertion.

FIG. 3 shows the warming catheter 5 fitted with the monorail sleeve 20 on the distal end of the catheter. The monorail sleeve is attached to the catheter near the curved coude tip 19. The monorail sleeve can be made of a flexible plastic material and attached to the catheter with adhesive or heat shrink material that will ensure that the monorail sleeve remains attached to the outer sleeve of the catheter. Alternative constructions such as co-extrusion may be used to manufacture the monorail sleeve. The monorail sleeve includes a monorail lumen 21 of appropriate diameter to closely fit over guidewire 22, which may be a standard sized guidewire, such as an 0.038" guidewire or may be a stylet or even an endoscope previously inserted to inspect the prostate and bladder. FIG. 4 shows an alternative embodiment of the monorail catheter of FIG. 3, in which the monorail lumen 21 is replaced by a short monorail tip lumen 23 disposed within the distal tip of the urethral warming catheter. FIG. 5 shows yet another alternative embodiment in which the monorail sleeve 24 extends the full length of the warming catheter. These constructions are variously referred to as monorail lumens, side saddle lumens, and side mount lumens, and the monorail tip construction is also referred to as a rapid exchange tip or RX tip. Each catheter may be inserted into the urethra over a guidewire which has already been inserted into the urethra. The guide wire is pushed through the urethra, past any obstruction and into the bladder. With the guide wire in place, the proximal end of the guidewire is threaded or back loaded through the monorail sleeve or monorail tip of the warming catheter. The warming catheter is then tracked over the guide wire, into the urethra up to and into the bladder, after which the guide wire may be removed or left in place.

Figure 6:
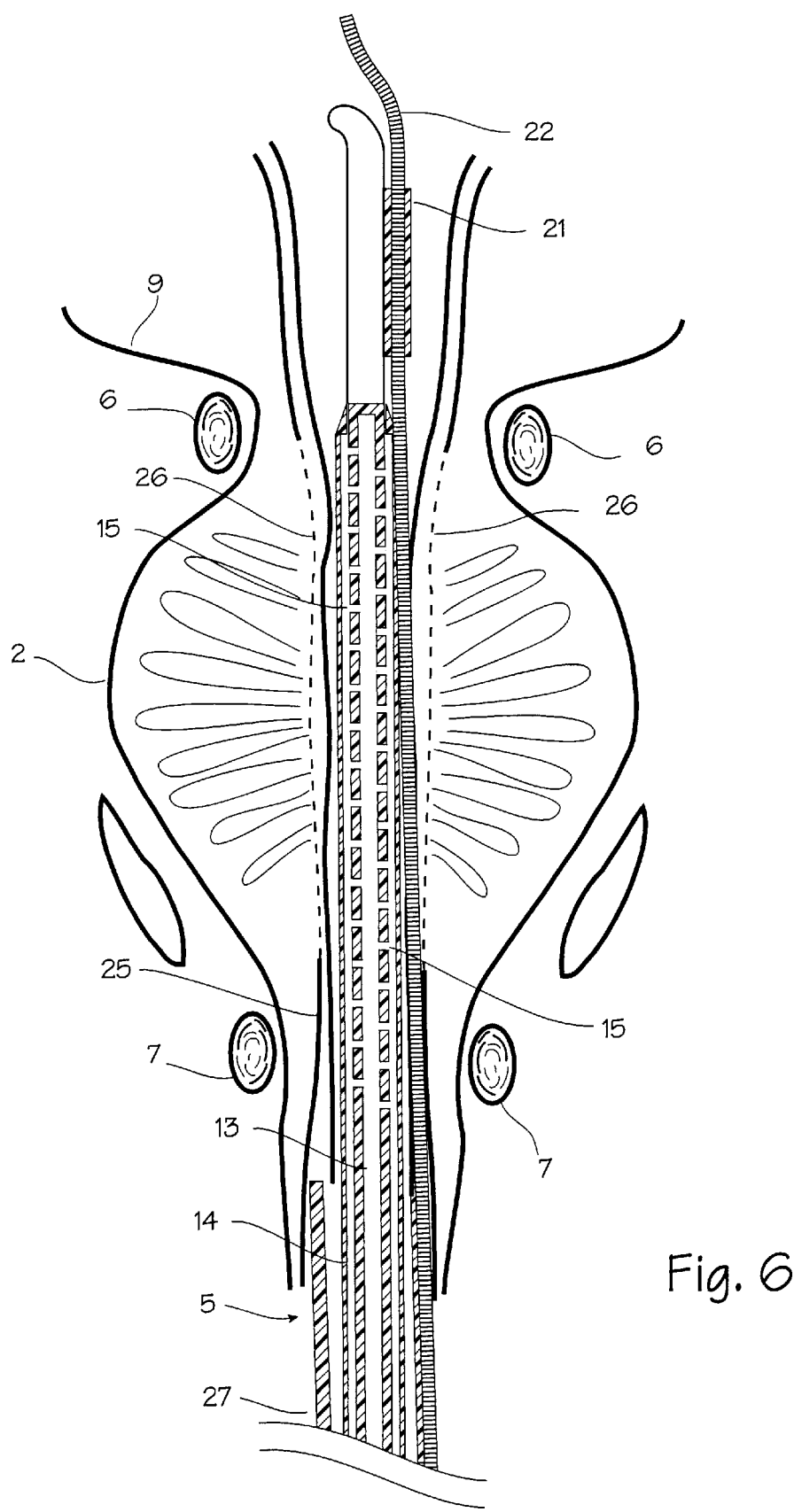
FIG. 6 a cross-sectional view of the warming catheter inserted through the urethra.

As shown in FIG. 1 and enlarged in FIG. 6, placement of the diffuser holes extends from the bladder neck sphincter 6 to the external sphincter 7. The diffuser holes allow some hot water to exit the inner lumen 13 and enter the outer lumen 14 near the external sphincter 7 and the distal portion 25 of the prostatic urethra. The holes may be of the same diameter and shape or the holes may be of varying diameter and shape. For example, the holes may be smaller at the proximal end and get larger at the distal end. This may be necessary to provide consistently increasing pressure through the distal segment of the outer lumen, thereby avoiding the possibility of a static condition at the distal end of the hot water supply lumen or the hot water return lumen 14. This ensures that some warming heat is applied to this area during cooling, and prevents the condition where all warming flow must pass through the proximal portion of the prostatic urethra and thereby lose all its heat before it reaches the distal portion of the prostatic urethra. The gradual enlargement of the holes accounts for any head loss in the small extra length of the flow path, and prevents all the hot warming fluid from short circuiting or bypassing the most distal portion of the warming segment. The exact size and gradation of the holes will depend upon numerous factors including the size of the lumens, the length of the warming section, the number of holes, the viscosity of the cooling fluid, etc., and can be calculated in accordance with fluid dynamic principles to obtain the desired flow pattern.

FIG. 6 more clearly illustrates the relationship between the catheter components and the anatomy of the prostate in which it will be used. The inner tube and inner lumen extend to about the bladder neck sphincter 6, as do the outer tube 11 and outer lumen 14. The diffuser holes 15 extend throughout the prostatic urethra, which is roughly delineated by dashed lines 26 extending from the bladder neck sphincter 6 to the external sphincter 7. The monorail sleeve is at the distal end of the warming catheter 5 near the curved coude tip, the guidewire having been threaded through the monorail sleeve. The air insulated outer sleeve 27 which is provided to prevent heat exchange between the hot water and areas of the urethra outside the prostate, extends from the proximal end of the catheter to the area just outside the external sphincter 7. The section of the warming catheter that lies within the prostate and prostatic urethra and corresponds to the diffuser ports holes 15 defines a warming section of the warming catheter. The remaining length of the catheter, both distal to the warming section and proximal to the warming section, need not be used for additional heat transfer to sections of the urethra not in danger of freezing during the cryosurgical process. This will lower the temperature and flow requirements for the warming catheter system. The inflow port 16 and handle may be insulated with appropriate insulation.

In use, the catheter is inserted through the patient's urethra to the bladder 9 and is connected to a hot fluid reservoir via the inlet port 16. The hot fluid (which may be water, saline solution, or other fluids including gases) is pumped into the inner lumen where it seeps through the diffuser holes into the outer lumen, thus warming the entire length of the prostatic urethra at the same time and approximately the same temperature. The fluid pressure keeps the hot fluid flowing and once the pressure is stabilized, continuous hot fluid reaches the distal end of the catheter as well as the proximal end, heating all the prostatic urethral tissue as a result. Hot fluid returns to the proximal end of the catheter through the outer lumen 13 and exits through the outflow port 17. The outflow port may be connected to a reservoir which is used to reheat the fluid and a recirculating pump which pumps reheated fluid back into the catheter. The result is that the hot fluid need not initially be extremely hot to accommodate for the heat gradient, thus reducing the risk of scalding the urethral tissue at the external sphincter in order to adequately heat the urethral tissue at the bladder neck sphincter. Also, the hot fluid pressure requirements are reduced since the diffuser holes stabilize the hot fluid pressure along the urethra, reducing pressure built up at the bladder neck sphincter, thus eliminating the risk of having the catheter burst at its sealed distal end. Hot fluid flow is continued during the cryosurgical process and for some time afterward to avoid freezing the warming catheter in place. After the prostate has warmed in accordance with the optimal medical procedure, the warming catheter and guidewire may be removed.

While the preferred embodiments of the devices and methods have been described in reference to the environment in which they were developed, they are merely illustrative of the principles of the inventions. The inventions have been described in the context of use during prostate cryosurgery, but the structures may find use in other surgical contexts and non-surgical areas. Other embodiments and configurations may be devised without departing from the spirit of the inventions and the scope of the appended claims.

We claim:

1. A method of treating a patient afflicted with a disease of the prostate, said method comprising:

providing a urethral warming catheter for warming the portion of the urethra in a male human patient bounded proximally by a bladder neck sphincter and distally by an external sphincter said, said urethral warming catheter having a distal section adapted for insertion into the portion of the urethra, said warming catheter comprising:

an outer tube the outside diameter of which approximates the inside diameter of the urethra, an inner tube which is within the outer tube, said inner tube opening into the outer tube near the distal section of the warming catheter;

wherein said inner tube has one or more diffuser holes communicating through the inner tube, said diffuser holes extending along the inner tube a distance approximating the length of the urethra which extends from the external sphincter to the bladder neck sphincter;

inserting the distal section of the urethral warming catheter into the urethra until the distal section is located within the prostate;

controlling the temperature of the portion of the urethra bounded proximally by the bladder neck sphincter and distally by the external sphincter by causing a fluid to flow distally through the inner tube, through the diffuser holes and into the outer tube, and then proximally through the outer tube;

ablating the prostate of the patient while controlling the temperature of the portion of the urethra bounded proximally by the bladder neck sphincter and distally by the external sphincter.

2. The method of claim 1 further comprising the steps of:

providing a monorail guidewire lumen on the warming catheter;

providing a guidewire adapted for use in the urethra;
inserting the guidewire into the urethra;
inserting the distal end of the warming catheter into the urethra by threading it over the guidewire and pushing it into and through the urethra over the guidewire.

3. The method of claim 1 further comprising the steps of:
providing a monorail tip guidewire lumen on the distal tip of the warming catheter;
providing a guidewire adapted for use in the urethra;
inserting the guidewire into the urethra;
inserting the distal end of the warming catheter into the urethra by threading the guidewire into the monorail tip guidewire lumen and pushing the warming catheter into and through the urethra over the guidewire.

4. The method of claim 1 further comprising the steps of:
providing a monorail guidewire lumen on the warming catheter, said monorail guidewire lumen extending substantially the entire length of the warming catheter;
providing a guidewire adapted for use in the urethra;
inserting the guidewire into the urethra;
inserting the distal end of the warming catheter into the urethra by threading the guidewire into the monorail guidewire lumen and pushing the warming catheter into and through the urethra over the guidewire.

5. The method of claim 1 further comprising the steps of:
providing an insulating jacket over the outer tube, said insulating jacket covering the outer tube along a proximal section of the outer tube.

6. A method of treating the prostate of a patient, said method comprising:
providing a warming catheter comprising:
a first tube disposed within the catheter defining a supply lumen communicating from the proximal end of the first tube to the distal end of the first tube;
a second tube defining a return lumen disposed coaxially about said supply lumen and forming with said supply lumen a fluid flow path extending from the proximal end of the catheter to the distal end of the catheter through the supply lumen and back to the proximal end of the catheter through the return lumen; and
wherein the first tube is provided with a plurality of diffuser holes located proximal to the distal end of said first tube and defining a flow path between the supply lumen and the return lumen, and said diffuser holes dispersed longitudinally along the first tube;
inserting the distal end of the urethral warming catheter into the urethra until the distal section is located within the prostate;
controlling the temperature of the prostatic urethra by causing a fluid to flow distally through the supply lumen, through the diffuser holes and into the return lumen, and then proximally through the return lumen;
ablating the prostate of the patient while controlling the temperature of the urethra.

7. The method of claim 6 further comprising the steps of:
providing a monorail guidewire lumen on the warming catheter;
providing a guidewire adapted for use in the urethra;
inserting the guidewire into the urethra;
inserting the distal end of the warming catheter into the urethra by threading it over the guidewire and pushing it into and through the urethra over the guidewire.

8. The method of claim 6 further comprising the steps of:
providing a monorail tip guidewire lumen on the distal tip of the warming catheter;
providing a guidewire adapted for use in the urethra;
inserting the guidewire into the urethra;
inserting the distal end of the warming catheter into the urethra by threading the guidewire into the monorail tip guidewire lumen and pushing the warming catheter into and through the urethra over the guidewire.

9. The method of claim 6 further comprising the steps of:
providing a monorail guidewire lumen on the warming catheter, said monorail guidewire lumen extending substantially the entire length of the warming catheter;
providing a guidewire adapted for use in the urethra;
inserting the guidewire into the urethra;
inserting the distal end of the warming catheter into the urethra by threading the guidewire into the monorail guidewire lumen and pushing the warming catheter into and through the urethra over the guidewire.

10. The method of claim 6 further comprising the steps of:
providing an insulating jacket over the second tube, said insulating jacket covering the second tube along a proximal section of the second tube.

11. A method of treating the prostate of a patient, said method comprising:
providing a warming catheter for use within the urethra, said warming catheter having a warming section of approximately the same length as the prostatic urethra the patient, and located longitudinally on the warming catheter near the distal tip of the warming catheter and in correspondence with the prostate when in place within the urethra, so that the warming section extends at least partially through the prostatic urethra to provide warming for the prostatic urethra, said warming catheter comprising:
a first tube disposed within the warming catheter and extending into the warming section, defining a supply lumen communicating from the proximal end of the first tube to the distal end of the first tube;
a second tube defining a return lumen disposed coaxially about said supply lumen and forming with said supply lumen a fluid flow path extending from the proximal end of the catheter to the distal end of the catheter through the supply lumen and back to the proximal end of the catheter through the return lumen; and
wherein the first tube is provided with plurality of diffuser holes located proximal to the distal end of said first tube and defining a flow path between the supply lumen and the return lumen, and said diffuser holes dispersed longitudinally along the first tube within the warming section of the warming catheter
inserting the distal end of the urethral warming catheter into the urethra until the warming section is located within the prostatic urethra;
controlling the temperature of the prostatic urethra by causing a fluid to flow distally through the supply lumen, through the diffuser holes and into the return lumen, and then proximally through the return lumen;
ablating the prostate of the patient while controlling the temperature of the prostatic urethra.

12. The method of claim 11 further comprising the steps of:
providing a monorail guidewire lumen on the warming catheter;

providing a guidewire adapted for use in the urethra;

inserting the guidewire into the urethra;

inserting the distal end of the warming catheter into the urethra by threading it over the guidewire and pushing it into and through the urethra over the guidewire.

13. The method of claim 11 further comprising the steps of:

providing a monorail tip guidewire lumen on the distal tip of the warming catheter;

providing a guidewire adapted for use in the urethra;

inserting the guidewire into the urethra;

inserting the distal end of the warming catheter into the urethra by threading the guidewire into the monorail tip guidewire lumen and pushing the warming catheter into and through the urethra over the guidewire.

14. The method of claim 11 further comprising the steps of:

providing a monorail guidewire lumen on the warming catheter, said monorail guidewire lumen extending substantially the entire length of the warming catheter;

providing a guidewire adapted for use in the urethra;

inserting the guidewire into the urethra;

inserting the distal end of the warming catheter into the urethra by threading the guidewire into the monorail guidewire lumen and pushing the warming catheter into and through the urethra over the guidewire.

15. The method of claim 11 further comprising the steps of: providing an insulating jacket over the outer tube, said insulating jacket covering the second tube along the length of the second tube proximal to the warming section of the warming catheter.

* * * * *